United States Patent [19]

Osusko

[11] Patent Number: 5,109,915
[45] Date of Patent: May 5, 1992

[54] TOOL AND INSPECTION-INSTRUMENT CARRIER FOR AN APPARATUS FOR EXAMINING OR REPAIRING A STEAM GENERATOR

[75] Inventor: Boris Osusko, Bad Schönborn, Fed. Rep. of Germany

[73] Assignee: ABB Reaktor GmbH, Mannheim, Fed. Rep. of Germany

[21] Appl. No.: 422,655

[22] Filed: Oct. 17, 1989

[30] Foreign Application Priority Data

Oct. 21, 1988 [DE] Fed. Rep. of Germany...8813215[U]

[51] Int. Cl.$^5$ .................. F22B 37/10; F16L 55/18; B25J 11/00
[52] U.S. Cl. .................. 165/11.2; 165/76; 901/1; 901/15; 901/44; 376/245; 414/728; 414/744.1
[58] Field of Search .......... 165/11.2, 76; 901/1, 901/44, 15; 376/245; 414/728, 744.1

[56] References Cited

U.S. PATENT DOCUMENTS

| | | |
|---|---|---|
| 3,934,731 | 1/1976 | Muller et al. |
| 4,663,727 | 5/1987 | Saporito et al. ............ 73/623 |

FOREIGN PATENT DOCUMENTS

| | | |
|---|---|---|
| 2263143 | 2/1977 | Fed. Rep. of Germany. |
| 8207968 | 10/1983 | France. |

Primary Examiner—John K. Ford

[57] ABSTRACT

An apparatus is disposed below a tube plate in a chamber of a steam generator which is accessible through a manhole, for examining and/or repairing steam-generator tubes in the tube plate. A tool or inspection-instrument carrier of the apparatus includes a pneumatic swivel cylinder detachably connected to the apparatus. The swivel cylinder has a housing and an output shaft. A feed unit is supported on the output shaft. A flexible shaft is axially movable by the feed unit. A compressed-air motor is associated with the housing for driving the flexible shaft.

3 Claims, 4 Drawing Sheets

TOOL AND INSPECTION-INSTRUMENT CARRIER FOR AN APPARATUS FOR EXAMINING OR REPAIRING A STEAM GENERATOR

The invention relates to a tool and/or inspection-instrument carrier for an apparatus which is disposed below a tube plate in a chamber of a steam generator which is accessible through a manhole, for examining and/or repairing the steam-generator tubes.

German Patent DE-PS 22 63 143 discloses such a carrier. In that device, the tools or inspection instruments are moved up to the tube plate through a conveying tube from outside the steam generator. The required movement inside the conveying tube can lead to trouble when the tools and inspection instruments are being inserted and removed. The conveying apparatus for the flexible shaft is disposed outside the steam-generator chamber so that long conveying distances have to be covered.

It is accordingly an object of the invention to provide a tool and inspection-instrument carrier for an apparatus for examining or repairing a steam generator, which overcomes the hereinafore-mentioned disadvantages of the heretofore-known devices of this general type, which provides a compact construction of the carrier, and which ensures trouble-free change-over of tools or inspection instruments.

With the foregoing and other objects in view there is provided, in accordance with the invention, in an apparatus disposed below a tube plate in a chamber of a steam generator accessible through a manhole for examining and/or repairing steam-generator tubes in the tube plate, a tool or inspection-instrument carrier, comprising a pneumatic swivel cylinder detachably connected to the apparatus, the swivel cylinder having a housing and an output shaft, a feed unit supported on the output shaft, a flexible shaft being axially movable by the feed unit, and a compressed-air motor associated with the housing for driving the flexible shaft.

The entire feed unit with the output shaft of the swivel cylinder, can be swivelled out of a working position extending in the axial direction of the tubes, to such an extent that the flexible shaft can be moved axially out of the manhole and out of the steam-generator chamber. The inspection instrument or tool is changed over in this position. The feed unit can then be swivelled into its working position again without difficulty. Despite its swivelling capacity, the carrier has a compact type of construction, which ensures that it can reach all positions of the tube plate, without requiring any conveying tube.

In keeping with the space-saving construction of the carrier, in accordance with another feature of the invention, the housing has a side facing toward and a side facing away from the compressed-air motor, and there is provided an exhaust-air filter supported on the side of the housing facing away from the compressed-air motor.

In accordance with an added feature of the invention, there is provided another compressed-air motor for moving the feed unit and a worm or angular gear associated with the other compressed-air motor, both being disposed between the housing and the feed unit.

In accordance with a concomitant feature of the invention, at least one of the swivel cylinder and/or the flexible shaft are hydraulically driven.

Other features which are considered as characteristic for the invention are set forth in the appended claims.

Although the invention is illustrated and described herein as embodied in a tool and inspection-instrument carrier for an apparatus for examining or repairing a steam generator, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

Figure 1:
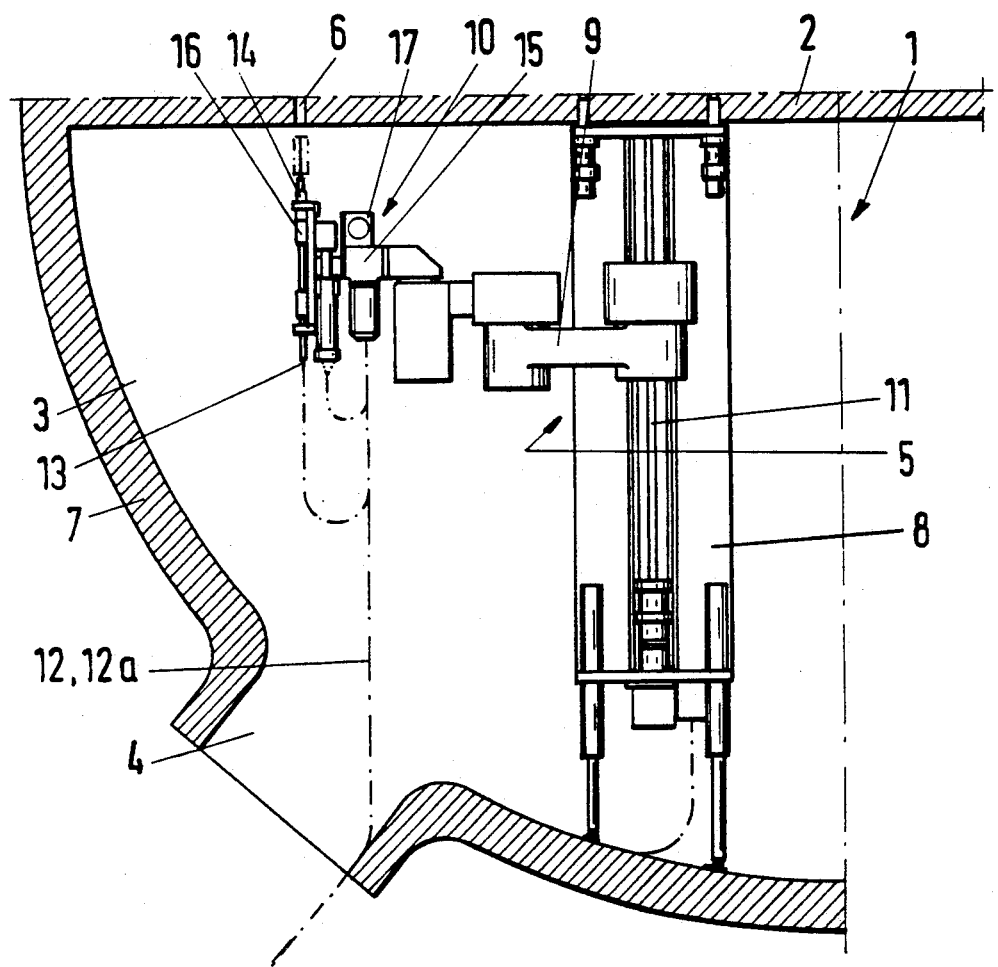
FIG. 1 is a fragmentary, diagrammatic, cross-sectional view of a steam generator with an apparatus and a tool and inspection-instrument carrier of the invention disposed in a steam-generator chamber.
Figure 5:
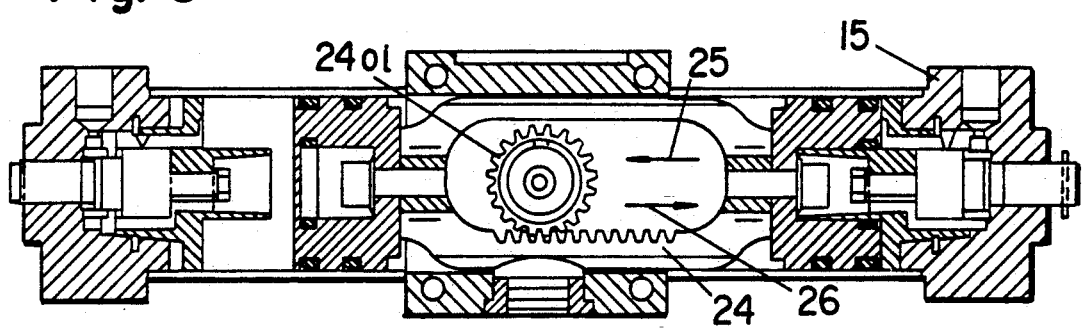
FIG. 5 is a longitudinal-sectional view of a swivel cylinder according to the invention.
Figure 2:
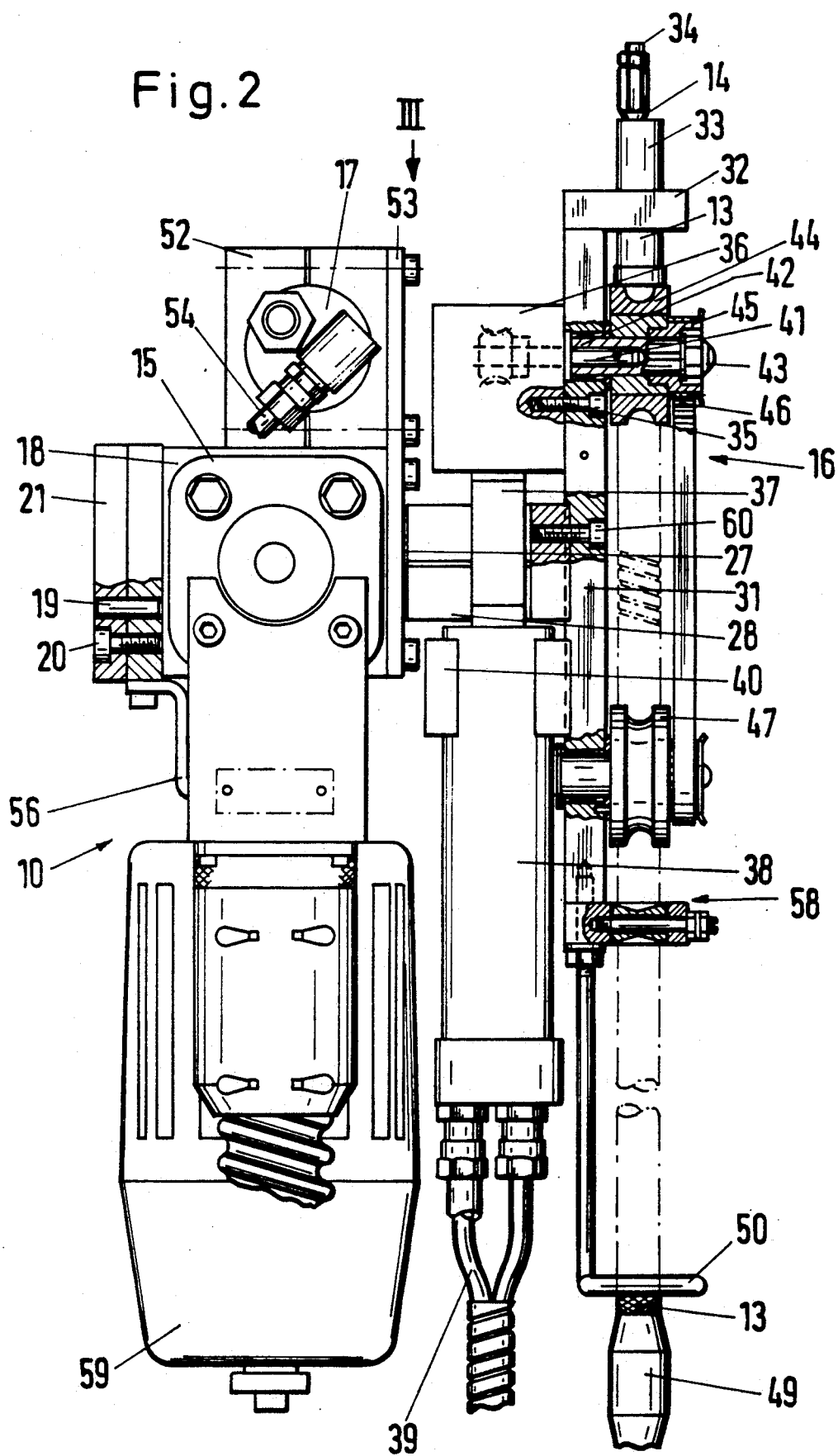
FIG. 2 is a fragmentary, partially broken-away, side-elevational view of the carrier on an enlarged scale.
Figure 3:
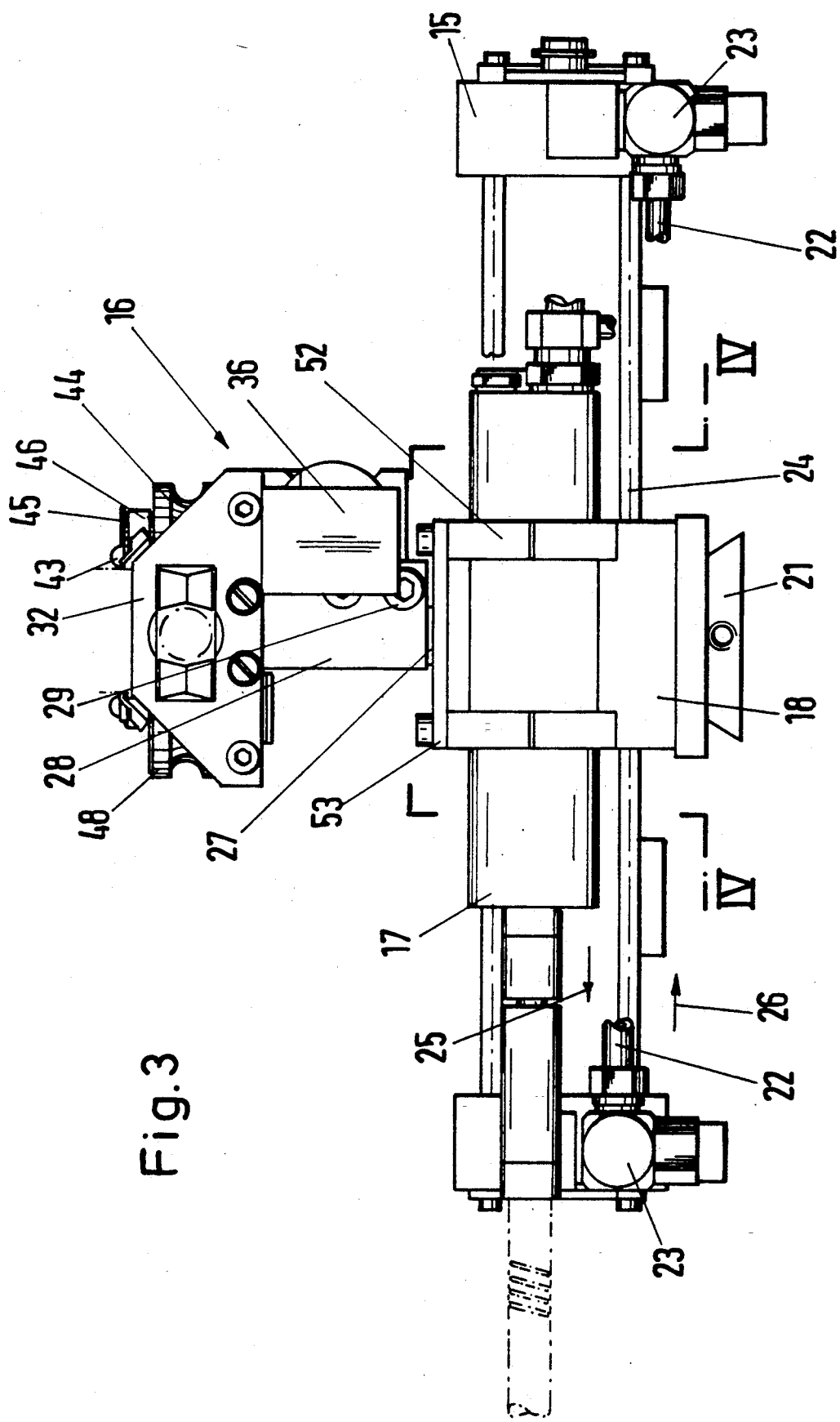
FIG. 3 is a top-plan view as seen in in the direction of an arrow III in FIG. 2.
Figure 4:
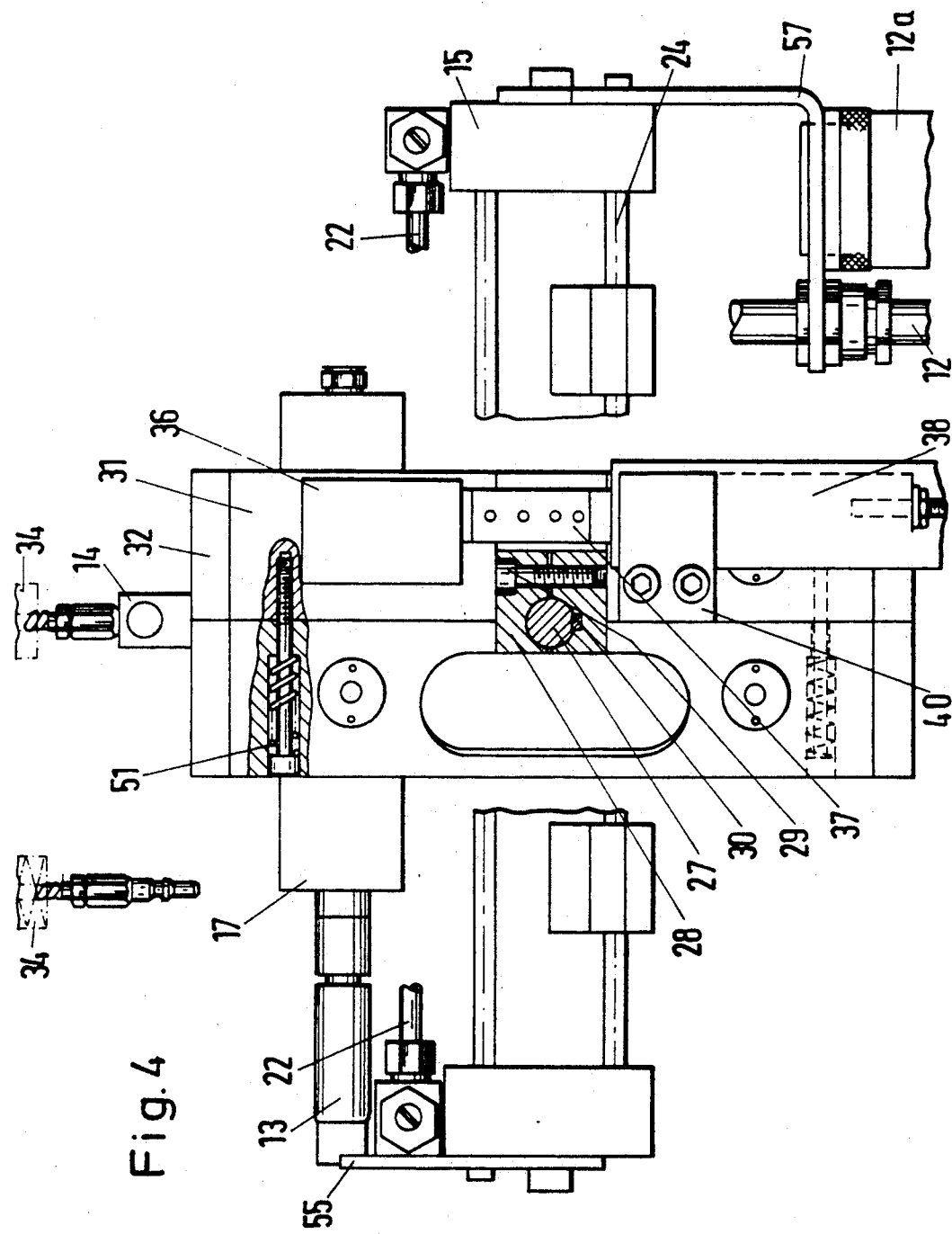
FIG. 4 is a fragmentary, partially broken-away, sectional view taken along line IV—IV in FIG. 3.

Referring now to the figures of the drawing in detail and first, particularly, to FIG. 1 thereof, there is seen a sectional area of a steam generator 1 with a tube plate or sheet 2 and a hemispherically bounded chamber 3. A manhole 4 passes through the hemispherically constructed wall 7 of the chamber 3 and permits introduction of an apparatus 5 for examining and/or repairing a tube 6 terminating in the tube plate 2. The apparatus is formed of an upright leg 8 extending between the tube plate 2 and the wall 7. Associated with the upright leg is an articulating arm 9 which is movable parallel to the tube plate. The end of the arm remote from the upright leg accommodates a carrier 10 for tools and/or inspection instruments. The articulating arm 9 can be moved in the vertical direction by means of a spindle drive 11 associated with the upright leg. Leading to the carrier 1 are supply lines 12, 12a for compressed air and current in order to set a flexible shaft 13 in rotation as well as to move it in its axial direction. The end of the flexible shaft 13 facing the tube plate 2 carries a quick-action coupling 14 for selectively accommodating various types of tools or inspection instruments. The carrier 10 is essentially formed of a swivel cylinder 15 which is detachably connected to the articulating arm 9, a feed unit 16 and a compressed-air motor 17 for driving the flexible shaft 13.

The interaction of the components of the carrier 10 to form a compact and space-saving apparatus will be explained with reference to FIGS. 2 to 5. The carrier 10, which is rotated through 180° in FIG. 2 relative to the representation in FIG. 1, is detachably connected to the articulating arm 9 shown in FIG. 1 through a coupling piece 21 connected to a housing 18 of the swivel cylinder 15 by pins 19 and screws 20. The swivel cylinder 15, which represents the supporting component of the carrier, has a compressed-air connection 22 shown in FIGS. 3 and 4 which is made with a one-way restrictor 23 connected therebetween. Depending on which side of the swivel cylinder 15 is controlled, a linear movement of a toothed rack 24 passing through the housing 18 is effected in the direction of arrows 25 or 26 and leads to a corresponding rotary movement of a pinion 24a disposed in the housing 18. The pinion is an integral part of an output shaft 27 leaving the housing 18. A split bearing block 28 makes a clamping connection with the output shaft 27 through screws 29 and a driving function is further assisted by a key-and-slot configuration 30. A mounting plate 31 of the feed unit 16 is fixed to the bearing block 28 through screws 60. Screwed to the mounting plate 31 is a bracket 32 through which the flexible shaft 13 passes. End piece 33 of the flexible shaft 13 contain the quick-action coupling 1 for accommodating a tool 34. Fixed to the mounting plate 31 through screws 35 is a worm gear 36 which is flexibly connected through a coupling piece 37 to a compressed-air motor 38. The compressed-air motor 38, which has a compressed-air connection 39, is likewise fixed to the mounting plate 31 by a motor holder 40. The compressed-air motor 38 and the worm gear 36 thereof are disposed in a space-saving manner due to an appropriate recess formed in the bearing block 28. A worm shaft 41 of the worm gear 36 passes through the mounting plate 31 and is pinned by a shaft 42 rotatably mounted in the mounting plate 31. A drive roller 44 and a toothed-belt wheel 45 which are components of the shaft 42, are secured with a cap nut 43. A further roller 47, which is likewise rotatably mounted on the mounting plate 31, is driven by a toothed belt 46. Disposed next to the rollers 44, 47 are guide rollers 48 which are likewise rotatably mounted on the mounting plate 31. The rollers 44, 47 and 48 together form the drive for driving the flexible shaft 13 in its axial direction. An idling roller 58 which is fixed to the mounting plate 31 interacts with a conical sleeve 49 sitting on the flexible shaft to form a limit switch for limiting the feed movement of the flexible shaft. A lifting handle 50 attached to the lower end of the mounting plate 31 serves to guide the flexible shaft. The two-piece construction of the mounting plate 31 enables the contact pressure of the rollers 44, 47, 48 on the flexible shaft 13 to be regulated with the help of springs 51. The compressed-air motor 17 is fixed to the housing 18 of the swivel cylinder 15 through a holder 53 and a clamping frame 52. The flexible shaft 13 is connected to the compressed-air motor 17 while maintaining adequate axial clearance of movement. The compressed-air motor, which has a compressed-air connection 54, provides the rotary drive for the flexible shaft 13. A shaft holder 55 which is screwed to the swivel cylinder 15, serves to support the flexible shaft 13 in the vicinity of the compressed-air motor 17. The housing 18 of the swivel cylinder 15 carries a retaining clip 56 which is screwed thereto, as well as an exhaust-air filter 59 for the compressed-air motors 17 and 38. The supply connections 12, 12a for current and compressed air are fixed to a lateral surface of the swivel cylinder 15 by a coupling holder 57.

If a tool or an inspection instrument is to be exchanged for another, a rotary movement of the output shaft 27 of the swivel cylinder 15 is performed. The feed unit 16 fixed to the output shaft 27 also performs the rotary movement until the feed unit has reached its change-over position at the level of the manhole 4, as controlled by the limit switch. The compressed-air motor 38 acts through the worm gear 36 to start the roller drive for the flexible shaft and guides the latter through the manhole out of the steam generator chamber so that a tool or inspection instrument can be changed over at that location without difficulty. Once the change-over has been made, the flexible shaft is returned again into the chamber so that it moves back into its working position below the tube plate through the rotation of the output shaft.

The foregoing is a description corresponding in substance to German Application G 88 13 215.3, dated Oct. 21, 1988, the International priority of which is being claimed for the instant application, and which is hereby made part of this application. Any material discrepancies between the foregoing specification and the aforementioned corresponding German application are to be resolved in favor of the latter.

I claim:

1. In an apparatus disposed below a tube plate in a chamber of a steam generator accessible through a manhole for examining and/or repairing steam-generator tubes in the tube plate, a tool or inspection-instrument carrier, comprising a pneumatic swivel cylinder detachably connected to the apparatus, said swivel cylinder having a housing and an output shaft, a feed unit supported on said output shaft, a flexible shaft being axially movable by said feed unit, and a compressed-air motor associated with said housing for driving said flexible shaft.

2. Tool and inspection-instrument carrier according to claim 1, wherein said housing has a side facing toward and a side facing away from said compressed-air motor, and including an exhaust-air filter supported on said side of said housing facing away from said compressed-air motor.

3. Tool and inspection-instrument carrier according to claim 1, including another compressed-air motor for moving said feed unit and a worm gear associated with said other compressed-air motor between said housing and said feed unit.

* * * * *